United States Patent [19]

Ko

[11] 4,322,407

[45] Mar. 30, 1982

[54] ELECTROLYTE DRINK

[75] Inventor: Sai Y. Ko, Burwood, Australia

[73] Assignee: Vitapharm Pharmaceutical Pty. Ltd., Moorabbin, Australia

[21] Appl. No.: 154,259

[22] Filed: May 29, 1980

Related U.S. Application Data

[63] Continuation-in-part of Ser. No. 86,098, Oct. 18, 1979, abandoned.

[30] Foreign Application Priority Data

Dec. 11, 1978 [AU] Australia .............................. PD7077

[51] Int. Cl.³ ..................... A61K 31/70; A61K 33/06;
A61K 33/14; A61K 33/42
[52] U.S. Cl. ................................... 424/128; 424/153;
424/154; 424/156; 424/157; 424/180; 424/263;
424/280

[58] Field of Search ............... 424/128, 153, 154, 156, 424/157, 180

[56] References Cited

PUBLICATIONS

Scientific Research, Jan. 20, 1969, p. 15.
The Pharmaceutical Journal, Bryan, vol. 169, p. 413.

*Primary Examiner*—Stanley J. Friedman
*Attorney, Agent, or Firm*—Sughrue, Mion, Zinn, Macpeak & Seas

[57] ABSTRACT

A chemical composition for reconstituting with water to provide an electrolyte drink intended for consumption by animals, especially human beings. The drink permits replacement of essential body constituents lost as a result of metabolic processes. The composition comprises $Na^+$, $K^+$, $Mg^{2+}$, $Cl^-$, $SO_4^{2-}$, $PO_4^{2-}$, citrate, sucrose, dextrose, ascorbic acid and pyridoxine.

9 Claims, No Drawings

ELECTROLYTE DRINK

CROSS-REFERENCE TO RELATED APPLICATIONS

This application is a continuation-in-part application of U.S. Patent Application Ser. No. 86,098, filed Oct. 18, 1979, now abandoned.

This invention relates to an electrolyte drink useful for replenishing the major constituents lost from body fluids as a result of metabolic processes. While the drink is mainly intended for use by humans and is described in that context, it is to be understood that it can equally be used by animals such as horses and dogs.

There are presently a substantial number of electrolyte drinks on the market which are alleged to replenish essential electrolytes and water lost from the body during physical activity. Such products are, however, generally unpalatable and do not, in fact, satisfy the body completely by replenishing all the essential constituents which are lost.

It is therefore an object of the invention to provide a drink which overcomes these defects and, furthermore, permits quick recovery of the body following strenuous activity.

The invention is based upon a number of new discoveries and known scientific data which can be summarized as follows:

(1) The unpleasant taste of electrolytes in drinks can be masked by carefully balancing the relative ratios of the electrolytes.

(2) Electrolytes in correct physiological quantities increase the efficiency of the body to utilize glycogen and improve muscular activities.

(3) Against the traditional concept that massive protein intake will efficiently increase muscular glycogen storage, experimentation in racing animals indicates that carbohydrates such as a simple combination of sucrose, glucose and citrate in the presence of electrolytes is a more efficient glycogen source. Carbohydrate as a glycogen source induces less stress in the metabolic system.

(4) The role of potassium is extremely important in oral electrolyte therapy to combat stress and in sugar absorption in the gastro intestinal tract. Clinical observations of racing animals and athletes performances indicates potassium deficiency is far more common. Supplementation in correct quantities and qualities reduces physical and metabolic stress and improves performance.

(5) Potassium other than in the form of potassium chloride induces potassium deficiency and alkalosis. Use of potassium citrate, gluconate, carbonate or phosphate as the potassium source is not suitable.

(6) Oral magnesium has to be provided at a level of three times the required theoretical level as only one third is absorbed through the intestine.

(7) Supplementation of pyridoxine in high doses and in combination with ascorbic acid greatly reduces the stress effect on the metabolic system of the body by increasing the metabolic "Purification" process in the liver and kidney.

(8) Buffer agents can improve glycogen utilization.

(9) Physical stress induces metabolic alkalosis and not metabolic acidosis as commonly believed. The presence of acid in the urine does not conclude the body is acidotic.

(10) Hydrated ions such as phosphate ions cannot be replaced by their chemically equivalent anhydrous salt. e.g. Sodium phosphate B.P. ($Na_2HPO_4.12-H_2O$) cannot be substituted by $Na_2HPO_4$ anhydrous. Experimentation indicates that although both are chemically identical when dissolved in water, they do not perform the same physiologically. The water of crystallisation in the case of sodium phosphate B.P. is chemically attached to the phosphate ion. It is in such a form that the intracellular substrate can utilize the phosphate as a buffer. Dissolving sodium phosphate anhydrous in water does not necessitate the attachment of water molecules to the phosphate ion. In fact this process of hydration is performed intracellularly, and requires energy. Ingestion of anhydrous sodium phosphate leads to additional stress on the intracellular substrate and dehydrates the cells. However if sodium phosphate B.P. is used as a source of phosphate and buffer, the intracellular substrate can utilize the available phosphate ion readily.

According to the present invention there is provided a mixture suitable for reconstituting with water to form a highly palatable drink which comprises sodium ions, potassium ions which have been derived from potassium chloride, magnesium ions, chloride ions, sulphate ions, phosphate ions as herein defined, citrate ions, sucrose, dextrose, ascorbic acid and pyridoxine, wherein the relative ratio of the ions sodium:potassium:magnesium:chloride:sulphate:phosphate is 5-7:3-5:1-3:5-6:1-3:5-7 calculated on a milliequivalent basis.

The phosphate ions referred to above and in the claims are defined as those ions which are produced upon the dissolution of hydrated disodium hydrogen phosphate and hydrated sodium dihydrogen phosphate in aqueous solution.

If desired a flavouring agent such as TRUSIL LEMON ELITE (the trade name of a commercial lemon flavouring agent supplied by Bush, Boake & Allan), may be incorporated in the mixture to provide a particularly pleasant flavour on the palate. Artificial sweeteners, colourings and preservatives may likewise be incorporated.

The phosphate and the citrate present in the mixture also function as a buffer system to maintain the drink within a desirable pH range. This pH range is preferably 6.8 to 7.4.

Preferably, the sucrose, dextrose and citrate is present in sufficient quantity to provide 3.4 Kcal of energy for every gram of mixture. This energy may be supplied by a mixture of 0.48 gram of sucrose, 0.318 gram of dextrose, 42 mg. of citric acid and 12 mg of sodium citrate.

The quantity of ascorbic acid is preferably 10 mg for every gram of concentrate and the pyridoxine is ideally present in an amount of 2.5 mg per gram of concentrate.

The drink which is produced from the mixture according to the present invention has the following properties:

(a) There is no saline taste as in conventional electrolyte drinks.

(b) It is a complete electrolyte replacement in the sense that it caters for the complete needs of the body physiologically. The electrolytes presented are balanced to the natural body daily requirement. This enables the body to absorb and use the electrolyte raw material to repair or replenish any deficiency and aid the body to quick recovery from stress.

(c) It contains a series of simple carbohydrates, viz. sucrose, dextrose and citrate, as a readily usable energy source. The body can make use of this immediately or build up the glycogen depot in the liver or muscles. The high glycogen level in the liver protects the liver and reduces cholesterol production.

(d) It provides a detoxifying effect mainly due to the presence of pyridoxine and ascorbic acid which aids the liver to efficiently metabolise and dispose unwanted harmful materials (alcohol, nitrogen waste etc.).

(e) The feeling of thirst, is stimulated both by a lower extracellular volume and a high plasma osmolarity. The present drink contains balanced electrolytes to provide for immediate adjustments, and hence satisfies the sensation of thirst.

(f) It provides potassium and sodium in its natural form of chlorides, and magnesium as sulphates as in the correct daily body requirement ratio. In addition, the phosphate rapidly helps to restore the body fluid to neutrality.

(g) It provides the blood with glucose. Unused glucose is automatically converted to glycogen and stored in the liver or muscle. It has generally been misunderstood that to increase glycogen storage to the maximum, vast quantities of protein should be ingested. However to convert protein to glycogen involves far more complicated and energy demanding metabolic processes. This is highly inefficient and wasteful of energy. In addition excess nitrogen waste from protein digestion also increases the demand, on the liver and kidney waste disposal system as excess nitrogen waste has to be dealt with to maintain the body free of metabolic alkalosis. In cases of potassium deficiency, the presence of ammonia enhances the metabolic alkalosis stress on the body buffering systems. In severe cases, this can be the major cause of kidney impairment. This fact has been repeatedly proven to be correct in racing greyhounds which have a diet consisting of a vast excess of meat and are subjected to severe racing stress.

(h) It improves the energy efficiency in the body. In Sydney University, athletes were required to perform a set work load in a given time under controlled laboratory conditions. Measurement of the heat generation by the body was used as a tool to measure the efficiency of the muscles to perform the work. The result was that the body temperature rise was significantly less when the present drink is ingested half an hour before the workout, as compared to a salt and dextrose mixture, water, fruit juice, beer and a known brand of electrolyte supplement. Body weight loss was also dramatically reduced.

(i) Potassium being a major intracellular component is provided in drink formulation. A depletion of potassium leads to a decrease in action potential of muscle and also causes metabolic alkalosis. The present drink overcomes this problem.

(j) It supplies the two natural body buffers, viz. the phosphate buffer and the citrate buffer.

(k) It counteracts the effect of alcohol by providing vitamins B6 and C to aid alcohol metabolism in liver, increasing glycogen storage in the liver which acts as a protectant, replacing electrolytes lost, restoring the glucose level in the blood which supplies the brain, providing buffers to aid alcohol by-product disposal and neutralising excess gastric hydrochloric acid secretion caused by alcohol irritation on the stomach wall.

(l) Diarrhoea and vomiting causes severe dehydration through loss of water and electrolytes. The present drink replenishes such losses and restores body fluid volume and osmolarity.

(m) It is a balanced mineral source.

A preferred embodiment of the invention will now be described in the following example.

EXAMPLE

A first mixture was prepared by blending 480 mg of disodium hydrogen phosphate ($Na_2HPO_4.12H_2O$) with 4.8 g of sucrose and 3.18 g of dextrose.

A second mixture was prepared by blending the following ingredients in the stated amounts.

Sodium Chloride:69.6 mg.
Potassium Chloride:288.0 mg.
Magnesium Sulphate (anhydrous):148.0 mg.
Sodium Citrate:120.0 mg.
Sodium Acid Phosphate:111.6 mg.
Ascorbic Acid:100.0 mg.
Pyridoxine Hydrochloride:25.0 mg.
Citric Acid:420.0 mg.
Lemon Flavouring:257.8 mg.

The two mixtures were then blended together and milled to 100 mesh to form a drink concentrate containing, for each 10 gm., 6.1 mEq sodium ions, 3.85 mEq potassium ions, 2.47 mEq magnesium ions, 5.0 mEq chloride ions, 2.47 mEq sulphate ions, 6.25 mEq phosphate ions, and 7.22 mEq citrate ions.

The product was a drink concentrate suitable for reconstituting with water to form a palatable drink.

I claim:

1. A mixture suitable for reconstituting with water to form a drink which comprises sodium ions, potassium ions which have been derived from potassium chloride, magnesium ions, chloride ions, sulphate ions, phosphate ions which have been derived from the dissolution of dodecahydrated disodium hydrogen phosphate and hydrated sodium dihydrogen phosphate in aqueous solution, citrate ions, sucrose, dextrose, ascorbic acid and pyridoxine, wherein the relative ratio of the ions sodium:potassium:magnesium:chloride:sulphate:phosphate is 5-7:3-5:1-3:5-6:1-3:5-7 calculated on a milliequivalent basis.

2. A mixture as claimed in claim 1 and including a flavouring agent.

3. A mixture as claimed in claim 1 and including an artificial sweetener and/or colouring and/or preservative.

4. A mixture as claimed in claim 1 which when reconstituted with water has a pH which is buffered within the range of 6.8 to 7.4.

5. A mixture as claimed in any one of claims 1-4 which contains a sufficient quantity of sucrose, dextrose and citrate to provide 3.4 Kcal of energy for every gram of mixture.

6. A mixture as claimed in any one of claims 1-4 wherein for every gram of mixture there is 0.48 gram of sucrose, 0.31 gram of dextrose and 7.22 milliequivalents of citrate.

7. A mixture as claimed in any one of claims 1-4 wherein for every gram of mixture there is 10 mg of ascorbic acid and 2.5 mg of pyridoxine.

8. A mixture suitable for reconstituting with water to form a drink which comprises 6.1 mEq sodium ions, 3.85 mEq potassium ions, 2.47 mEq magnesium ions, 5.0 mEq chloride ions, 2.47 mEq sulphate ions, 6.25 mEq phosphate ions which have been derived from the dissolution of dodecahydrated disodium hydrogen phosphate and hydrated sodium dihydrogen phosphate in aqueous solution, 7.22 mEq citrate ions, 100 mg ascorbic acid, 25 mg pyridoxine, 4.8 g sucrose, 3.1 g dextrose, and lemon flavouring q.s. per 10 grams of mixture.

9. A drink concentrate which comprises an admixture of sodium chloride, potassium chloride, anhydrous magnesium sulphate, dodecahydrated disodium hydrogen phosphate, hydrated sodium dihydrogen phosphate, dextrose, sucrose, ascorbic acid, pyridoxine hydrochloride, sodium citrate, citric acid and lemon flavoring, present for each 10 grams of concentrate in the following amounts sodium chloride:69.6 mg.
potassium chloride:288.0 mg.
magnesium sulphate:148.0 mg.
sodium citrate:120.0 mg.
disodium hydrogen phosphate:480.0 mg.
sodium dihydrogen phosphate:111.6 mg.
ascorbic acid:100.0 mg.
pyridoxine hydrochloride:25.0 mg.
citric acid:420.0 mg.
sucrose:4.8 gm.
dextrose:3.18 gm.
lemon flavouring:257.8 mg.

* * * * *